United States Patent
Neji et al.

(10) Patent No.: US 10,948,558 B2
(45) Date of Patent: Mar. 16, 2021

(54) METHOD OF PERFORMING MAGNETIC RESONANCE IMAGING AND A MAGNETIC RESONANCE APPARATUS

(71) Applicants: Siemens Healthcare Limited, Camberley (GB); King's College London, London (GB)

(72) Inventors: Radhouene Neji, London (GB); Sebastien Roujol, Kingston upon Thames (GB); Rene Botnar, London (GB)

(73) Assignees: King's College, London, London (GB); Siemens Healthcare GmbH, Erlangen (DE)

( * ) Notice: Subject to any disclaimer, the term of this patent is extended or adjusted under 35 U.S.C. 154(b) by 370 days.

(21) Appl. No.: 16/108,531

(22) Filed: Aug. 22, 2018

(65) Prior Publication Data

US 2019/0064294 A1    Feb. 28, 2019

(30) Foreign Application Priority Data

Aug. 22, 2017    (GB) ..................................... 1713444

(51) Int. Cl.
*G01R 33/50*    (2006.01)
*A61B 5/055*    (2006.01)
(Continued)

(52) U.S. Cl.
CPC ............ *G01R 33/50* (2013.01); *A61B 5/0456* (2013.01); *A61B 5/055* (2013.01); *A61B 5/7289* (2013.01);
(Continued)

(58) Field of Classification Search
CPC .. G01R 33/50; G01R 33/543; G01R 33/5673; G01R 33/5659; G01R 33/246; A61B 5/055; A61B 5/7289; A61B 5/0456
See application file for complete search history.

(56) References Cited

U.S. PATENT DOCUMENTS

| 2011/0001476 A1* | 1/2011 | Morrell ............... G01R 33/5659 324/309 |
| 2014/0200436 A1* | 7/2014 | Weingartner .......... A61B 5/055 600/413 |

(Continued)

OTHER PUBLICATIONS

Weiskopf et al., "Unified segmentation based correction of R1 brain maps for RF transmit field inhomogeneities (UNICORT)," NeuroImage, vol. 54, 2011, pp. 2116-2124 (2011).

(Continued)

*Primary Examiner* — Patrick Assouad
*Assistant Examiner* — Haidong Zhang
(74) *Attorney, Agent, or Firm* — Schiff Hardin LLP

(57) ABSTRACT

In a method of performing magnetic resonance imaging and a magnetic resonance apparatus, first MR data are acquired of a region of interest of a subject in the absence of a B1 field. Second MR data are acquired of the region of interest in the presence of a B1 field, and within a short time interval after generation of the B1 field. The first and second MR data are processed to determine a B1 field map, and a T1 map is generated using the B1 field map. The T1 map is a B1 corrected T1 map. The first and second MR data 103, 109 may be acquired as part of a T1 mapping sequence, such as a MOLLI or SASHA type cardiac T1 mapping sequence.

14 Claims, 2 Drawing Sheets

(51) Int. Cl.
    *G01R 33/54*     (2006.01)
    *A61B 5/0456*     (2006.01)
    *G01R 33/565*     (2006.01)
    *G01R 33/24*     (2006.01)
    *A61B 5/00*     (2006.01)
    *G01R 33/567*     (2006.01)

(52) U.S. Cl.
    CPC ......... *G01R 33/246* (2013.01); *G01R 33/543* (2013.01); *G01R 33/5659* (2013.01); *G01R 33/5673* (2013.01)

(56) References Cited

U.S. PATENT DOCUMENTS

| | | | | |
|---|---|---|---|---|
| 2014/0364721 | A1* | 12/2014 | Lee | A61B 5/4836 |
| | | | | 600/411 |
| 2015/0160320 | A1* | 6/2015 | Chow | G01R 33/50 |
| | | | | 324/309 |
| 2018/0003788 | A1* | 1/2018 | Shinoda | G01R 33/543 |

OTHER PUBLICATIONS

Castro et al., "Template method to improve brain segmentation from inhomogeneous brain magnetic resonance images at high fields," 2010 7th IEEE International Symposium on Biomedical Imaging: From Nano to Macro, Rotterdam, Netherlands, pp. 73-76 (2010).

\* cited by examiner

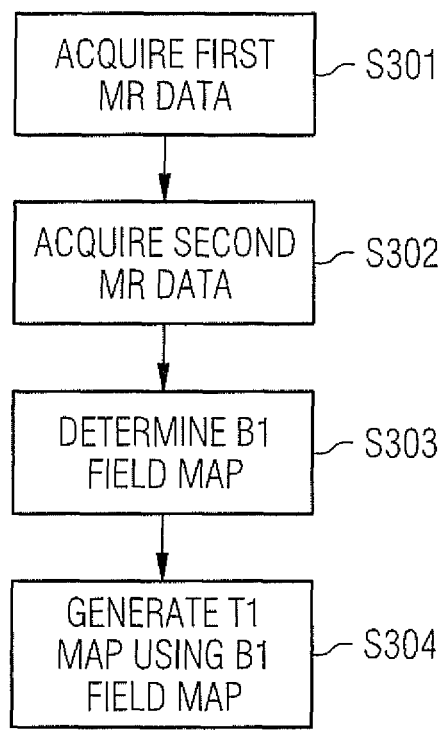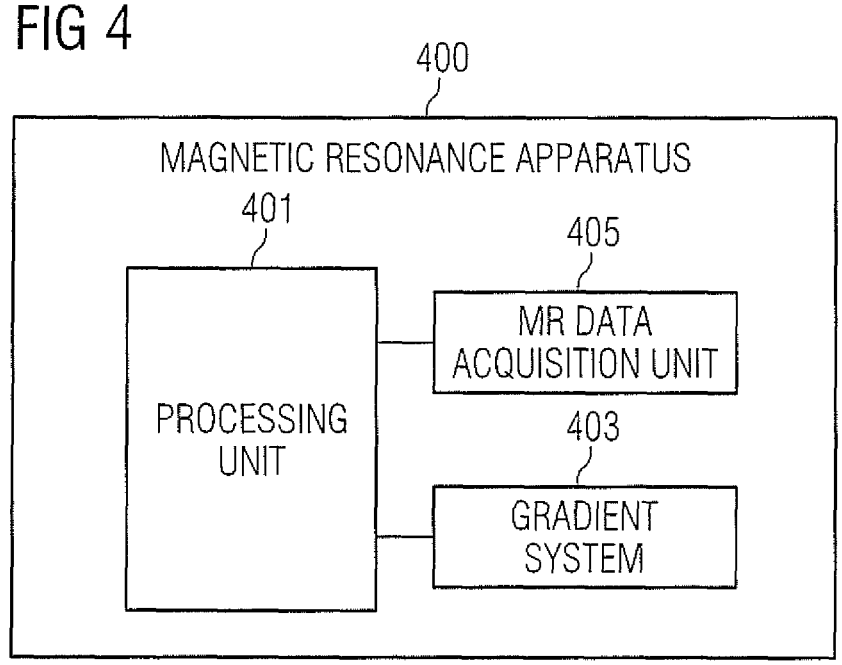

METHOD OF PERFORMING MAGNETIC RESONANCE IMAGING AND A MAGNETIC RESONANCE APPARATUS

BACKGROUND OF THE INVENTION

Field of the Invention

The present invention relates to a method of performing magnetic resonance imaging and a magnetic resonance apparatus. In particular, the present invention relates to a method of performing magnetic resonance imaging and a magnetic resonance apparatus for generating a T1 map.

Description of the Prior Art

T1 relaxation time, also known as the spin-lattice or longitudinal relaxation time, is a measure of how fast the nuclear spin magnetization returns to its equilibrium state after an excitation pulse. T1 is a key source of soft tissue contrast in MRI.

Generating a T1 map of an examination area is a useful tool for a medical professional to identify diseases in soft tissue that affect T1. T1 mapping is useful to characterize diffuse or infiltrative myocardial diseases, including cardiomyopathies, myocarditis, and amyloidosis.

T1 mapping, and in particular cardiac T1 mapping, may be performed using specialized pulse sequences.

One such specialized pulse sequence is commonly known as the Modified Look-Locker inversion recovery (MOLLI) which may be used for myocardial T1 mapping. In an example MOLLI sequence, a 180 degrees inversion pulse is generated followed by the acquisition of five images. The 180 degrees inversion pulse and the image acquisitions are ECG triggered. The five images are acquired after successive heartbeats during the diastole period of the cardiac cycle. After the acquisition of the five images, there is a rest period of 3 heartbeats, before the sequence is repeated for three heartbeats.

The resultant images may then be sorted in order of increasing inversion time (TI) and the signal intensity in each pixel of the image may be fit onto an apparent T1 recovery curve during a T1 fitting process. The apparent T1 recovery curve may follow a three-parameter model $S(t)=A-B \exp(-t/T1^*)$ where $S(t)$ is the signal intensity at inversion time t. A, B and $T1^*$ are the parameters to be estimated by the curve fitting. $T1^*$ is the apparent recovery time rather than the true, actual recovery time T1. T1 can be calculated by applying the correction $T1=T1^*(B/A-1)$. After computing the T1 for each pixel, a T1 map for the region of interest may be generated.

Another such specialized pulse sequence is commonly known as the Saturation-Recovery-Single-Shot Acquisition (SASHA) which may also be used for myocardial T1 mapping. SASHA is also ECG triggered, and within each cardiac cycle during the SASHA sequence, a 90 degree saturation pulse is generated followed by an image acquisition. In SASHA, each of the images is acquired at the same point in the cardiac cycle, but with different times after the application of the saturation pulse.

The resultant images may then be sorted in order of increasing saturation time and the signal intensity in each pixel of the image may be fit onto a T1 recovery curve during a T1 fitting process. The fitting process may use a two-parameter fitting model, defined by $S(t)=A(1-\exp(-t/T1))$ or may use a three-parameter fitting model $S(t)=A-B \exp(-t/T1)$. Where A, B and T1 are parameters to be estimated by the curve fitting. After computing the T1 for each pixel, a T1 map for the region of interest may be generated.

The T1 mapping procedure of MOLLI and SASHA may be affected by B1 inhomogeneity—that is variation in the B1 field generated by the RF coil of the MRI scanner. The B1 inhomogeneity may affect both the generation of the preparation pulses, and also the acquisition of the images. B1 inhomogeneity may affect the T1 mapping process leading to inaccurate T1 values being determined.

One existing method to account for B1 inhomogeneity includes applying adiabatic or optimized preparation pulses or a train of preparation pulses. Such preparation pulses may act to minimize sensitivity to B1 inhomogeneity in the imaging pulses.

Another existing method to account for B1 inhomogeneity includes modifying the T1 fitting process to include an additional parameter that aims to model saturation or inversion efficiency, and signal disturbances caused by imaging pulses.

SUMMARY OF THE INVENTION

It is an object of the present disclosure to provide an improved, or at least an alternative, way of taking into account B1 inhomogeneity.

According to a first aspect of the invention, a method of performing magnetic resonance (MR) imaging includes acquiring first MR data of a region of interest of a subject, the first MR data being acquired in the absence of a B1 field; acquiring second MR data of the region of interest, the second MR data being acquired in the presence of a B1 field, and within a short time interval after generation of the B1 field; processing the first and second MR data to determine a B1 field map; and generating a T1 map using the B1 field map.

Here, "in the absence of a B1 field" may mean that a preparation pulse is not applied prior to acquiring the first MR data. The acquiring of the first MR data may be performed at the start of an MR scan. The acquiring of the first MR data may be performed during a MR scan provided sufficient time is allowed to elapse after the generation of an excitation pulse such that substantially full recovery of the magnetization has occurred when the first MR data is acquired. The sufficient time may be around 5 times T1. The sufficient time may be around 3 seconds. Generally, acquiring the first MR data at the start of the MR scan is preferred. Generally, the absence of a B1 field means that the net magnetization of the region of interest lies along the direction of the applied main magnetic field B0. There may be no transverse (MX or MY magnetization), and instead only a longitudinal component (MZ) may be present. This may also be referred to as being in equilibrium magnetization M0.

Here, acquiring second MR data "within a short time interval after generation of the B1 field" means that the second MR data is acquired within the minimal amount of time possible after generating the B1 field in order to minimize T1 relaxation effects on the B1 estimation. The specific minimal time may depend on factors such as the nature of an excitation pulse used to generate the B1 field, and the specifics of the MR apparatus being used. The second MR data may be acquired as quickly as possible after the generation of the B1 field so as to minimize the T1 relaxation effects. The second MR data may be acquired within less than 40 ms, less than 30 ms, or less than 20 ms after generating the B1 field. The second MR data may be acquired within 10-30 ms, or 20-30 ms after generating the B1 field.

Advantageously, the present invention is able to determine a B1 field map, and use this B1 field map in the generation of the T1 map. As a result, the present invention is able to take into account the effect of any B1 inhomogeneity during the T1 mapping process. The present invention is thus able to generate a B1-corrected T1 map that provides more accurate, precise, and/or reliable T1 map estimates.

The present invention therefore avoids the need to use adiabatic or optimized preparation pulses. Such pulses do not account for the B1 effects of the imaging pulses and may increase the specific absorption rate. In addition, this existing approach depends on the B1 amplitude, which means that the adiabatic condition may not be reached in regions which experience a large drop in B1 amplitude. The present disclosure therefore avoids the need to include an additional parameter for modelling saturation or inversion efficiency, and signal disturbances caused by imaging pulses. Such an additional fitting parameter may increase the noise in the T1 map. Instead, the present disclosure actually determines the B1 inhomogeneity and uses this to generate a B1-corrected T1 map.

Generating the T1 map may be implemented by acquiring MR data using a T1 mapping sequence, and using the acquired MR data and the B1 field map to generate the T1 map. The B1 field map may be used in a two/three parameter model fitting procedure.

The first MR data and/or the second MR data may be acquired as part of the T1 mapping sequence. The second MR data may be acquired during one of the cardiac cycles of a T1 mapping sequence such as MOLLI of SASHA. Significantly, this means that the implementation of the present invention is simple because only the scan for acquiring the first MR data needs to be added to the T1 mapping sequence.

The first MR data and/or the second MR data may be acquired during a separate sequence to the T1 mapping sequence. This may be implemented by performing an image registration process to align the first and second MR data with the MR data acquired during the T1 mapping sequence. This may include interpolating the first and second MR data to the higher resolution of the MR data acquired for T1 mapping for the T1 mapping process.

Processing the first and second MR data to determine a B1 field map may include determining the signal ratio of the first MR data to the second MR data, and using the determined signal ratio to determine the B1 field map. In particular, the signal ratio may be used to determine the B1 field map according to the equation:

$$\frac{S_p}{S_r} = (\cos\alpha - 1) * \exp\left(-\frac{TD}{T1}\right) + 1 \sim \cos\alpha$$

where Sp is the signal intensity value for the first MR data, Sr is the signal intensity value for the second MR data, α is the flip angle, and TD refers to the difference in time between the inversion or saturation pulse and the acquisition of the k-space center. In particular, the B1 field map can be obtained by taking the inverse cosine of the signal ratio if T1 relaxation during TD is neglected.

Acquiring the second MR data may be implemented by generating an excitation pulse to generate the B1 field, and acquiring the second MR data within a short time interval after the generation of the excitation pulse. The excitation pulse may be a preparation pulse.

The preparation pulse may be an inversion pulse, and the second MR data may be acquired within a short inversion time after the generation of the inversion pulse.

The inversion pulse may be generated as part of a modified Look-Locker Inversion recovery (MOLLI) type pulse sequence.

The inversion pulse may be generated as part of a shortened modified Look-Locker Inversion recovery (ShMOLLI) type pulse sequence.

The preparation pulse may be a saturation pulse, and the second MR data may be acquired within a short saturation time after the generation of the saturation pulse.

The saturation pulse may be generated as part of a Saturation-Recovery-Single-Shot Acquisition (SASHA) type pulse sequence.

The first MR data/second MR data may be MR image data/MR images. The method may include generating first and second images from the first MR data/second MR data.

The method may be used in cardiac T1 mapping, such as for myocardial imaging. The region of interest may be all or part of the subject's heart, and the T1 map may be a cardiac T1 map.

The method may use centric k-space scanning. The use of centric k-space scanning may help to minimize the delay for the MR scan used to acquire the second image.

The acquiring of the first MR data and/or the second MR data may be triggered by an ECG signal.

According to a second aspect of the invention, a magnetic resonance (MR) apparatus has an MR data acquisition unit to acquire first MR data of a region of interest of a subject, the first MR data being acquired in the absence of a B1 field, and to acquire second MR data of the region of interest, the second MR data being acquired in the presence of a B1 field, and within a short time interval after generation of the B1 field; and a processing unit operable to process the first and second MR data to determine a B1 field map, and operable to generate a T1 map using the B1 field map.

The MR apparatus may be operable to perform the method of the first aspect of the invention.

According to a third aspect of the invention, a non-transitory computer readable medium is encoded with programming instructions (program code that, when executed by a computer or computer system or a processor, cause the computer or computer system or processor to perform the method of the first aspect of the invention).

BRIEF DESCRIPTION OF THE DRAWINGS

FIG. 3 shows a process diagram for an example method according to the first aspect of the present invention.

FIG. 4 shows an example MR apparatus according to the second aspect of the present invention.

DESCRIPTION OF THE PREFERRED EMBODIMENTS

Figure 1:
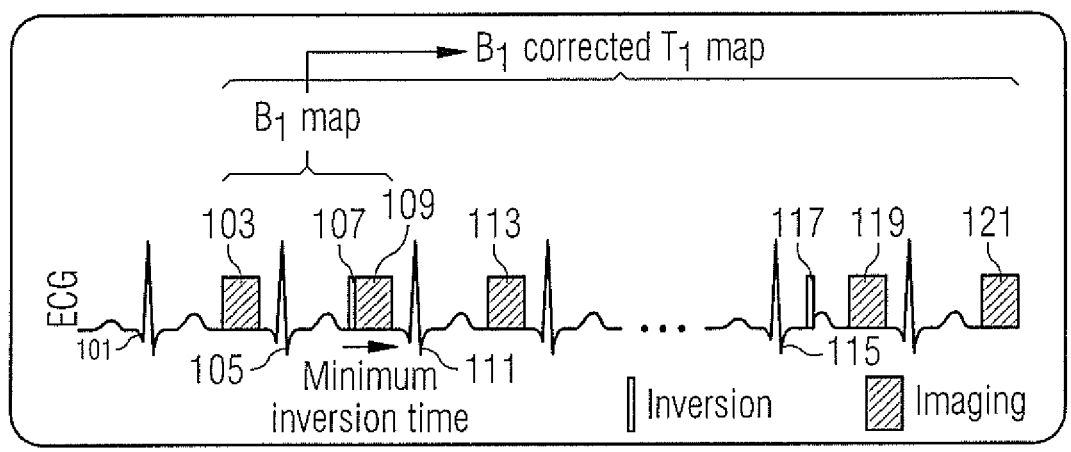
FIG. 1 shows a sequence diagram for generating a B1-corrected T1 map using a MOLLI type sequence according to aspects of the present invention.

Referring to FIG. 1, there is shown a sequence diagram for generating a B1 corrected T1 map in accordance with aspects of the present invention. The sequence diagram is used for myocardial T1 mapping and is ECG gated.

The sequence starts by acquiring first MR data 103 in the absence of a B1 field. Acquiring the first MR data 103 is triggered by the ECG pulse 101. The sequence continues by acquiring second MR data 109 in the presence of a B1 field, and within a short time after generation of the B1 field. Acquiring the second MR data 109 is triggered by the ECG pulse 105, which, in this example, is the ECG pulse immediately following ECG pulse 101. This means that the second MR data 109 are acquired in the next heartbeat after the heartbeat during which the first MR data 103 are acquired. The B1 field is generated by an inversion pulse 107, and the second MR data 109 are acquired within minimum inversion time following the inversion pulse 107. The minimum inversion time may be 30 ms or less.

The acquired first and second MR data 103, 109 are processed to determine a B1 field map. In particular, the signal ratio of the first and second MR data 103, 109 is determined and this signal ratio is used to determine the B1 field map. In one example, the signal ratio is used to determine the B1 field map according to the equation:

$$\frac{S_p}{S_r} = (\cos\alpha - 1) * \exp\left(-\frac{TD}{T1}\right) + 1 \sim \cos\alpha$$

Here, Sp is the signal intensity value for the first MR data, Sr is the signal intensity value for the second MR data, α is the flip angle, and TD refers to the difference in time between the inversion or saturation pulse and the acquisition of the k-space center. This method of calculating a B1 field map is disclosed, for a different application, in Fautz, H. P., et al. "B1 mapping of coil arrays for parallel transmission." *Proceedings of the 16th Annual Meeting of ISMRM*, Toronto, Canada. 2008. The contents of which is herein incorporated by reference.

The acquiring of the first and second MR data 103, 109 in FIG. 1 is incorporated into a MOLLI type sequence used for cardiac T1 mapping. The inversion pulse 107 and second acquisition of MR data 109 are the first stage of the MOLLI sequence. The MOLLI sequence continues by generating four additional MR data 113 in an ECG gated manner, that is in response to ECG pulses 111, such that five MR data are acquired over five heartbeats following the generation of the inversion pulse 107. Following a rest period of three heartbeats, another inversion pulse 117 is generated in response to an ECG pulse 115, and a further three MR data 119, 121 are acquired in an ECG gated manner such that a further three MR data 119, 121 are acquired over three heartbeats.

The resultant MR data 103, 109, 113, 119, 121 are MR images, and are sorted in order of increasing inversion time (TI). For T1 mapping, the signal intensity in each pixel of the image is fit onto an apparent T1 recovery curve during a T1 fitting process. Significantly, the fitting process takes into account the B1 field map determined from the first and second MR data 103, 109 such that the B1 effects relating to the preparation and the imaging pulses are modelled during the fitting process. This means that the T1 map is a B1-corrected T1 map.

In the example of FIG. 1, the acquiring the first and second MR data 103, 109 is integrated into the MOLLI sequence used for T1 mapping. This is generally preferred because it means that it requires minimal modification to existing MOLLI sequences. Only the scan for acquiring the first MR data 103 needs to be added to the T1 mapping sequence, and the acquiring of the second MR data 109 needs to be done with minimal inversion time.

The acquiring of the first and second MR data 103, 109 does not have to be integrated into the MOLLI sequence used for T1 mapping. Instead, the first and second MR data 103, 109 may also be acquired during a separate scan. In such examples, the first and second MR data 103, 109 may be acquired with the same or a lower spatial resolution than the T1 mapping sequence so as to minimize T1 effects during the readout train. As a result, the first and second MR data 103, 109 may need to be interpolated to the higher resolution of the MR data acquired for T1 mapping. An image registration process may also need to be performed to align the first and second MR data 103, 109 with the MR data acquired during the T1 mapping sequence.

Figure 2:
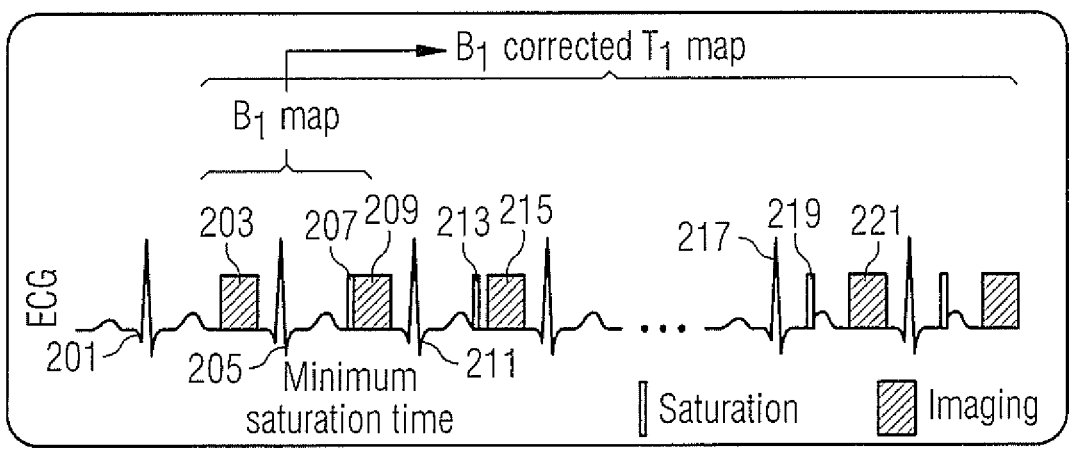
FIG. 2 shows a sequence diagram for generating a B1-corrected T1 map using a SASHA type sequence according to aspects of the present invention.

Referring to FIG. 2, there is shown a sequence diagram for generating a B1 corrected T1 map in accordance with aspects of the present disclosure. The sequence diagram is used for myocardial T1 mapping and is ECG gated.

The sequence starts by acquiring first MR data 203 in the absence of a B1 field. Acquiring the first MR data 203 is triggered by the ECG pulse 201. The sequence continues by acquiring second MR data 209 in the presence of a B1 field, and within a short time after generation of the B1 field. Acquiring the second MR data 209 is triggered by the ECG pulse 205, which, in this example, is the ECG pulse immediately following ECG pulse 201. This means that the second MR data 209 are acquired in the next heartbeat after the heartbeat during which the first MR data 203 are acquired. The B1 field is generated by a saturation pulse 207, and the second MR data 209 are acquired within minimum saturation time following the saturation pulse 207. The minimum saturation time may be 30 ms or less.

The acquired first and second MR data 203, 209 are processed to determine a B1 field map in the same way as discussed above for FIG. 1.

The acquiring of the first and second MR data 203, 209 is incorporated into a SASHA type sequence used for cardiac T1 mapping. The saturation pulse 207 and acquiring second MR data 209 are the first stage of the SASHA sequence. The SASHA sequence continues by generating further saturation pulses 213, 219 in an ECG-gated manner, such that the saturation pulses are generated in response to ECG pulses 211, 217. In particular, within each cardiac cycle, a saturation pulse 213, 219 is generated followed by the acquisition of MR data 215, 221. The MR data 215, 221 are all acquired at the same point in the cardiac cycle, but with different times after the application of the saturation pulse 213, 219. This is because the saturation pulses 213, 219 are generated at different points during the cardiac cycle.

The acquired MR data 203, 209, 215, 221 are MR images. For T1 mapping, the MR images are sorted in order of increasing saturation time and the signal intensity in each pixel of the image is fit onto a T1 recovery curve during a T1 fitting process. Significantly, the fitting process takes into account the B1 field map determined from the first and second MR data 203, 209 such that the B1 effects relating to the preparation and the imaging pulses are modelled during the fitting process. This means that the T1 map is a B1-corrected T1 map.

In the example of FIG. 2, the acquiring the first and second MR data 203, 209 is integrated into the SASHA sequence used for T1 mapping. This is generally preferred because it means that it requires minimal modification to existing SASHA sequences. Only the scan for acquiring the first MR data 203 needs to be added to the T1 mapping sequence, and the acquiring of the second MR data 209 needs to be done with minimal saturation time.

The acquiring of the first and second MR data 203, 209 does not have to be integrated into the SASHA sequence used for T1 mapping. Instead, the first and second MR data 203, 209 may also be acquired during a separate scan. In such examples, the first and second MR data 203, 209 may be acquired with the same or a lower spatial resolution than the T1 mapping sequence to as to minimize T1 effects during the readout train. As a result, the first and second MR data 203, 209 may need to be interpolated to the higher resolution of the MR data acquired for T1 mapping. An image registration process may also need to be performed to align the first and second MR data 203, 209 with the MR data acquired during the T1 mapping sequence.

The present disclosure is not limited to MOLLI and SASHA type T1 mapping sequences. For example, a ShMOLLI type sequence is within the scope of the present disclosure.

Referring to FIG. 3, there is shown an example method according to the first aspect of the invention.

Step 301 involves acquiring first MR data of a region of interest of a subject, the first MR data being acquired in the absence of a B1 field.

Step 302 involves acquiring second MR data of the region of interest, the second MR data being acquired in the presence of a B1 field, and within a short time interval after generation of the B1 field.

The first and second MR data may be acquired using the pulse sequence diagrams described above in relation to FIGS. 1 and 2.

Step 303 involves processing the first and second MR data to determine a B1 field map.

Step 304 involves generating a T1 map using the B1 field map. The generated T1 map is a B1 corrected T1 map, in which the effects of B1 inhomogeneity are taken into account. Generating the T1 map may involve performing a Bloch simulation of the whole sequence, including modelling of the B1 effects of both preparation and imaging pulses. This can be used for a more accurate and reproducible T1 fitting. Other ways for generating the T1 map are within the scope of the present invention.

Referring to FIG. 5, there is shown an example MR apparatus 400 according the second aspect of the disclosure. The MR apparatus 400 has a processor 401, a gradient system 403, and an MR data acquisition unit 405 (scanner).

The MR data acquisition unit 405 is designed to acquire MR data. In particular, the MR data acquisition unit 405 acquires first MR data of a region of interest of a subject, the first MR data being acquired in the absence of a B1 field, and acquires second MR data of the region of interest, the second MR data being acquired in the presence of a B1 field, and within a short time interval after generation of the B1 field. The processor 401 is operable to process the first and second MR data to determine a B1 field map, and is operable to generate a T1 map using the B1 field map.

The MR data acquisition unit 405 includes an excitation system. The excitation system radiates an excitation pulse, such as an inversion or saturation pulse, into the subject and receive signals from the subject. The excitation system includes a transmitter (not shown) and a receiver (not shown). The excitation system can be an RF system with one or more RF coils (not shown).

The MR apparatus 400 includes a magnet (not shown) for establishing a stationary magnetic field. The magnet can be a permanent magnet, a superconducting magnet or other type of magnet.

The processor 401 is in communication with the MR data acquisition unit 405, and the gradient system 403, so as to control these components. The processor 401 is configured to execute program code for controlling the MR apparatus 400 in order to perform the method of the first aspect of the invention. The processor 401 can be an integrated component of the MR apparatus 400. The processor 401 can be a component of a desktop computer, a workstation, a server, or a laptop computer.

According to another aspect of the invention, a non-transitory computer-readable storage medium is encoded with that, instructions when executed by the processor 401, cause the processor 401 to perform the method of the first aspect of the invention.

At least some of the exemplary embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, as an example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements.

The described embodiments are to be considered as illustrative and not restrictive in character, it being understood that only the preferred embodiments have been shown and described and that all changes and modifications that come within the scope of the inventions as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" is used the item can include a portion and/or the entire item unless specifically stated to the contrary.

In summary, there is provided a method of performing magnetic resonance imaging and a magnetic resonance apparatus. First MR data 103 is acquired of a region of interest of a subject in the absence of a B1 field. Second MR data 109 is acquired of the region of interest in the presence of a B1 field, and within a short time interval after generation of the B1 field. The first and second MR data 103, 109 are processed to determine a B1 field map, and a T1 map is generated using the B1 field map. The first and second MR data 103, 109 may be acquired as part of a T1 mapping sequence, such as a MOLLI or SASHA type cardiac T1 mapping sequence.

All of the features disclosed herein, and/or all of the steps of any method or process disclosed herein, may be combined in any combination, except combinations where at least some of such features and/or steps are mutually exclusive.

Each feature disclosed herein may be replaced by alternative features serving the same, equivalent or similar purpose, unless expressly stated otherwise. Thus, unless expressly stated otherwise, each feature disclosed is one example only of a generic series of equivalent or similar features.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method of performing magnetic resonance (MR) imaging, comprising:
   acquiring first MR data of a region of interest of a subject, the first MR data being acquired in the absence of a B1 field;
   acquiring second MR data of the region of interest, the second MR data being acquired in the presence of a B1 field, and within a minimal amount of time possible after generation of the B1 field;
   processing the first and second MR data to determine a B1 field map, wherein processing the first and second MR data to determine a B1 field map comprises determining the signal ratio of the first MR data to the second MR data, and using the determined signal ratio to determine the B1 field map; and
   generating a T1 map using the B1 field map.

2. A method as claimed in claim 1, wherein generating the T1 map comprises acquiring MR data using a T1 mapping sequence, and using the acquired MR data and the B1 field map to generate the T1 map.

3. A method as claimed in claim 2, wherein the first MR data and the second MR data are acquired as part of the T1 mapping sequence.

4. A method as claimed in claim 2, wherein the first MR data and the second MR data are acquired during a separate sequence to the T1 mapping sequence.

5. A method as claimed in claim 1, wherein the second MR data is acquired no more than 30 ms after generation of the B1 field.

6. A method as claimed in claim 1, wherein acquiring the second MR data comprises generating an excitation pulse to generate the B1 field, and acquiring the second MR data within a minimal amount of time interval possible after the generation of the excitation pulse.

7. A method as claimed in claim 6, wherein the excitation pulse is a preparation pulse.

8. A method as claimed in claim 7, wherein the preparation pulse is an inversion pulse, and wherein the second MR data is acquired within a minimal amount of inversion time possible after the generation of the inversion pulse.

9. A method as claimed in claim 8, wherein the inversion pulse is generated as part of a modified Look-Locker inversion recovery (MOLLI) type pulse sequence.

10. A method as claimed in claim 7, wherein the preparation pulse is a saturation pulse, and wherein the second MR data is acquired within a minimal amount of saturation time possible after the generation of the saturation pulse.

11. A method as claimed in claim 10, wherein the saturation pulse is generated as part of a Saturation-Recovery-Single-Shot Acquisition (SASHA) type pulse sequence.

12. A method as claimed in claim 1, wherein the region of interest is all or part of the subject's heart, and the T1 map is a cardiac T1 map.

13. A magnetic resonance (MR) apparatus comprising:
    an MR data acquisition unit to acquire first MR data of a region of interest of a subject, the first MR data being acquired in the absence of a B1 field, and to acquire second MR data of the region of interest, the second MR data being acquired in the presence of a B1 field, and within a minimal amount of time possible after generation of the B1 field; and
    a processor configured to process the first and second MR data to determine a B1 field map, and to generate a T1 map using the B1 field map,
    wherein the processing the first and second MR data to determine a B1 field map comprises determining the signal ratio of the first MR data to the second MR data, and using the determined signal ratio to determine the B1 field map.

14. A non-transitory, computer-readable data storage medium encoded with programming instructions, said storage medium being loaded into a computer system of a magnetic resonance (MR) apparatus, and said programming instructions causing said computer system to:
    operate the MR apparatus to acquire first MR data of a region of interests of a subject, said first MR data being acquired in the absence of a B1 field, and to acquire second MR data of the region of interests, said second MR data being acquired in the presence of a B1 field, and within a minimal amount of time possible after generation of the B1 field;
    process the first and second MR data to determine a B1 field map by determining the signal ratio of the first MR data to the second MR data, and using the determined signal ratio to determine the B1 field map; and
    generate a T1 map using the B1 field map.

* * * * *